US012629101B2

(12) United States Patent
Lim et al.

(10) Patent No.: US 12,629,101 B2
(45) Date of Patent: May 19, 2026

(54) APPARATUS AND METHOD FOR DIAGNOSING DEVELOPMENTAL DISORDERS

(71) Applicant: LumanLab Inc., Sejong-si (KR)

(72) Inventors: Jae Hyun Lim, Seoul (KR); So Yoon Jung, Seoul (KR)

(73) Assignee: LumanLab Inc., Sejong-si (KR)

( * ) Notice: Subject to any disclaimer, the term of this patent is extended or adjusted under 35 U.S.C. 154(b) by 0 days.

(21) Appl. No.: 18/922,562

(22) Filed: Oct. 22, 2024

(65) Prior Publication Data

US 2025/0127459 A1     Apr. 24, 2025

(30) Foreign Application Priority Data

Oct. 23, 2023     (KR) ........................ 10-2023-0141941

(51) Int. Cl.
*A61B 5/00*          (2006.01)
*G16H 50/20*        (2018.01)

(52) U.S. Cl.
CPC .......... *A61B 5/7267* (2013.01); *A61B 5/0077* (2013.01); *A61B 5/4803* (2013.01);
(Continued)

(58) Field of Classification Search
CPC ....... A61B 5/7267; G16H 50/20; G16H 10/20
See application file for complete search history.

(56) References Cited

U.S. PATENT DOCUMENTS 6,322,503 B1 *  11/2001  Sparhawk, Jr. ........  G09B 19/00
                                                                          600/300
2022/0369976 A1  11/2022  Abbas et al.
2024/0257974 A1   8/2024  Wall et al.

FOREIGN PATENT DOCUMENTS

KR      10-2023-0085964 A     6/2023
WO           2023149653 A1     8/2023

OTHER PUBLICATIONS

"Machine learning for early detection of autism (and other conditions) using a parental questionnaire and home video screening" by H. Abbas et al. 2017 IEEE Int Conf Big Data. pp. 3558-3561 (Year: 2017).*
"Machine Learning Based Autism Spectrum Disorder Detection from Videos" by Wu et al. 2020 IEEE Int Conf E-health Net, App, Serv. (Year: 2020).*

(Continued)

*Primary Examiner* — Jason M Ip

(74) *Attorney, Agent, or Firm* — ZION IP; Byungwoong Park

(57)          ABSTRACT

An apparatus and method for diagnosing developmental disorder using an artificial neural network are disclosed. An apparatus for diagnosing developmental disorders according to one exemplary embodiment includes a communication unit that performs communication with one or more user terminals and a control unit connected to the communication unit, in which the control unit receives at least one of image data and voice data for an analysis target from the user terminal and performs a first developmental disorder diagnosis through one or more artificial neural networks learned to perform a developmental disorder diagnosis, receives questionnaire response data from the user terminal and performs a second developmental disorder diagnosis according to predetermined standard, and generates developmental disorder diagnosis data for the analysis target based on the first developmental disorder diagnosis and the second developmental disorder diagnosis.

13 Claims, 5 Drawing Sheets

(52) U.S. Cl.
CPC .......... *G16H 50/20* (2018.01); *A61B 2503/04*
(2013.01); *A61B 2503/06* (2013.01)

(56)                    References Cited

OTHER PUBLICATIONS

Examination report No. 1 for standard patent application of AU, issued on Sep. 30, 2025.
Office Action of KIPO, issued on Dec. 8, 2025.
Halim Abbas, "Machine learning approach for early detection of autism by combining questionnaire and home video screening", May 7, 2018.

* cited by examiner

APPARATUS AND METHOD FOR DIAGNOSING DEVELOPMENTAL DISORDERS

CROSS-REFERENCE TO RELATED APPLICATIONS

This application claims the priority of Korean Patent Application No. 10-2023-0141941 filed on Oct. 23, 2023, in the Korean Intellectual Property Office, the disclosure of which is incorporated herein by reference.

BACKGROUND

Field

The present disclosure relates to an apparatus and method for diagnosing developmental disorders using an artificial neural network.

Description of the Related Art

In a method for diagnosing developmental disorders using a questionnaire, parents directly evaluate how proficient their children are in developmental evaluation items, and thus, there is a problem that the results vary depending on the subjective judgment of the parents. Accordingly, technology for diagnosing developmental disorders using an artificial neural network has been actively studied recently. Korean Patent Publication No. 10-2023-0085964 discloses a method and analysis device for predicting future brain nerve developmental disorders using F-18 FDG PET images of newborns based on a machine learning model.

SUMMARY

An object of the present disclosure is to provide an apparatus and method for diagnosing developmental disorders using an artificial neural network.

According to an aspect, there is provided an apparatus for diagnosing developmental disorders, the apparatus including: a communication unit that performs communication with one or more user terminals; and a control unit connected to the communication unit, in which the control unit receives at least one of image data and voice data for an analysis target from the user terminal and performs a first developmental disorder diagnosis through one or more artificial neural networks learned to perform a developmental disorder diagnosis, receives questionnaire response data from the user terminal and performs a second developmental disorder diagnosis according to predetermined standard, and generates developmental disorder diagnosis data for the analysis target based on the first developmental disorder diagnosis and the second developmental disorder diagnosis.

The control unit may transmit diagnosis guide data for the developmental disorder diagnosis to the user terminal, and receive at least one of image data and voice data corresponding to the diagnosis guide data.

The control unit may receive training data that includes at least one of learning image data and learning voice data for one or more users using the artificial neural network and includes correct answer values for each of the learning image data and learning voice data to perform a first learning diagnosis, perform a second learning diagnosis according to a predetermined standard based on one or more questionnaire training data, and perform first learning of the artificial neural network by comparing the first learning diagnosis and the second learning diagnosis for the same person.

The control unit may update the artificial neural network using the corresponding learning image data and learning voice data when the first learning diagnosis and the second learning diagnosis for the same person are the same.

When the first learning diagnosis and the second learning diagnosis for the same person are different, and the correct answer value is compared with the first learning diagnosis and the second learning diagnosis for the same person and the first learning diagnosis is the same as the correct answer value, the control unit may update the artificial neural network using the corresponding learning image data and learning voice data.

When the first learning diagnosis and the second learning diagnosis for the same person are different, and the correct answer value is compared with the first learning diagnosis and the second learning diagnosis for the same person and the second learning diagnosis is the same as the correct answer value, the control unit may exclude the corresponding learning image data and learning voice data from the training data.

The control unit may perform a first developmental disorder diagnosis on at least one of the image data and voice data for the analysis target received from the user terminal using a first-learned artificial neural network, perform a second developmental disorder diagnosis according to predetermined standard based on questionnaire response data received from the user terminal, and generate developmental disorder diagnosis data by assigning predetermined weights to each of the first developmental disorder diagnosis and the second developmental disorder diagnosis.

The control unit may generate developmental disorder diagnosis data based on the first developmental disorder diagnosis when the first developmental disorder diagnosis and the second developmental disorder diagnosis are different.

The control unit may further generate notification data notifying that diagnosis results are different when the first developmental disorder diagnosis and the second developmental disorder diagnosis are different.

The control unit may perform a re-diagnosis for items with different disorder diagnosis results when the first developmental disorder diagnosis and the second developmental disorder diagnosis are different.

The control unit may further receive disease data for the analysis target, and set the predetermined weight differently according to the disease data.

The control unit may transmit the image data, voice data, and questionnaire response data for the analysis target received from the user terminal to a user terminal of a medical expert, receive expert developmental disorder diagnosis data from the user terminal of the medical expert, and perform secondary learning of the artificial neural network using the first developmental disorder diagnosis when the first developmental disorder diagnosis and expert developmental disorder diagnosis are the same.

The control unit may derive a receiver operating characteristic (ROC) for the first-learned artificial neural network and an ROC for the second-learned artificial neural network, maintain the first-learned artificial neural network when an area under the ROC Curve (AUC) of the first-learned artificial neural network is greater than an AUC of the second-learned artificial neural network, and replace the first-learned artificial neural network with the second-learned artificial neural network when the AUC of the second-learned artificial neural network is greater.

According to aspect, there is provided a method for diagnosing developmental disorders performed by a computing device including one or more processors and a memory storing one or more programs executed by the one or more processors, the method including: receiving at least one of image data and voice data for an analysis target from a user terminal and performing a first developmental disorder diagnosis through one or more artificial neural networks learned to perform a developmental disorder diagnosis, receiving questionnaire response data from the user terminal and performing a second developmental disorder diagnosis according to predetermined standard, and generating developmental disorder diagnosis data for the analysis target based on the first developmental disorder diagnosis and the second developmental disorder diagnosis.

The accuracy of diagnosis can be improved by analyzing the image and voice data through the artificial neural network.

The accuracy of diagnosis can be improved by providing the guide for data acquisition and improving the quality of acquired data.

The accuracy of diagnosis result can be improved by learning and selecting the artificial neural network based on sensitivity/specificity.

DETAILED DESCRIPTION OF EXEMPLARY EMBODIMENT

Hereinafter, an exemplary embodiment of the present disclosure will be described in detail with reference to the attached drawings. In explaining the present disclosure, when it is judged that a specific description of a related known function or configuration may unnecessarily obscure the gist of the present disclosure, the detailed description will be omitted. In addition, the terms described below are terms defined in consideration of the functions in the present disclosure, and may vary depending on the intention or custom of the user or operator. Therefore, the definitions should be made based on the contents throughout the present specification.

Hereinafter, exemplary embodiments of an apparatus and method for diagnosing developmental disorders diagnosis will be described in detail with reference to the drawings.

Figure 1:
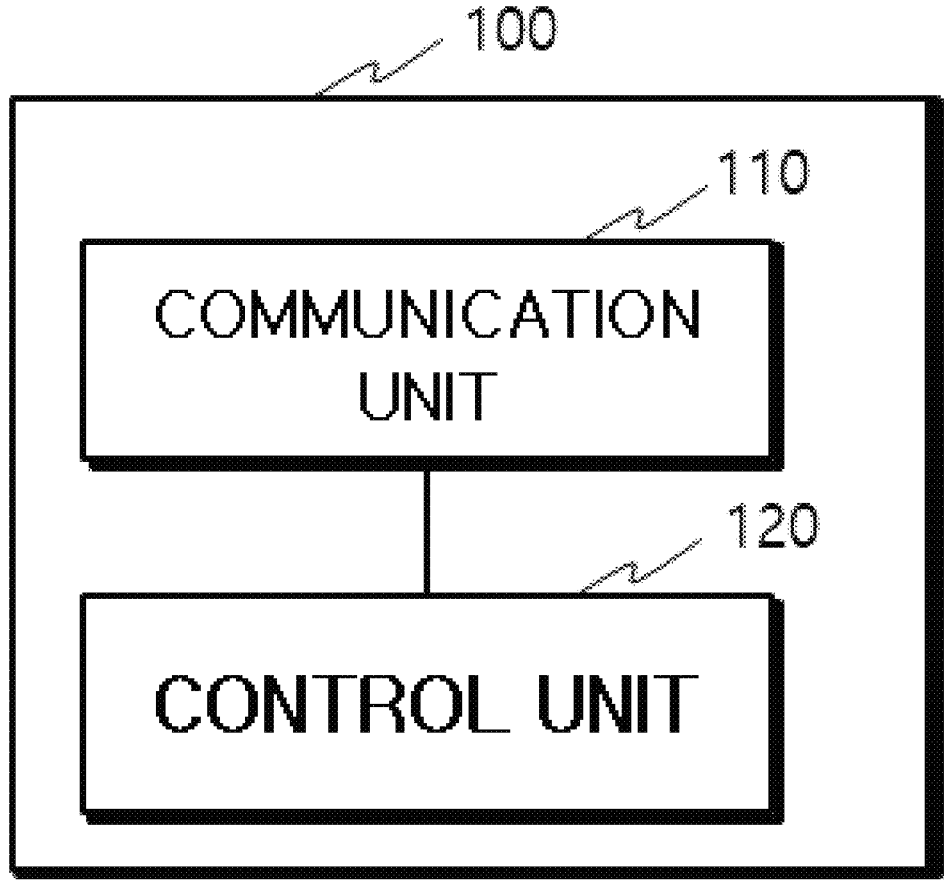
FIG. 1 is a configuration diagram of an apparatus for diagnosing developmental disorders according to one exemplary embodiment.
Figure 2:
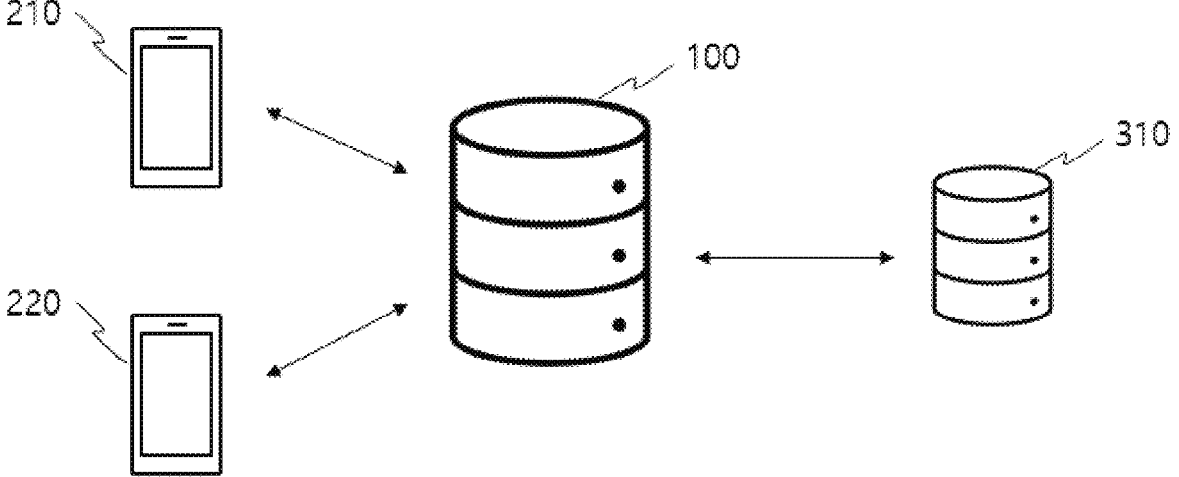
FIG. 2 is a configuration diagram for explaining an operating environment of the apparatus for diagnosing developmental disorders according to one exemplary embodiment.

FIG. 1 is a configuration diagram of an apparatus for diagnosing developmental disorders according to one exemplary embodiment.

Referring to FIG. 1, an apparatus 100 for diagnosing developmental disorders may include a communication unit

110 that performs communication with one or more user terminals and a control unit 120 connected to the communication unit 110.

As an example, the apparatus 100 for diagnosing developmental disorders may perform developmental disorder diagnosis for infants or toddlers based on an artificial neural network based on observation data obtained from a user terminal 210 of the guardian of the infant or toddler. For example, the observation data may include at least one of image data, voice data, and questionnaire response data written by the guardian for a predetermined item.

The apparatus 100 for diagnosing developmental disorders may firstly provide the calculated diagnosis result data to the guardian of the infant or toddler, thereby supporting the determination of the possibility of developmental disorder and the need for response for the infant or toddler. In addition, the apparatus 100 for diagnosing developmental disorders may secondarily provide the observation data and diagnosis result data to a medical expert, obtain feedback on this, and update the diagnosis result verification and the artificial neural network model.

As an example, the apparatus 100 for diagnosing developmental disorders may include an artificial neural network learned using "observation and diagnosis data of developmental disorders of other infants and toddlers by month" as training data. In this case, the training data may include the diagnosis result of the medical expert for the observation data as a correct answer value, and the diagnosis result and the correct answer value may be compared to perform first learning of the artificial neural network.

After that, the apparatus 100 for diagnosing developmental disorders may update the first learned artificial neural network model using the first diagnosis result and the medical expert's feedback for the child to generate a second artificial neural network model.

Figure 3:
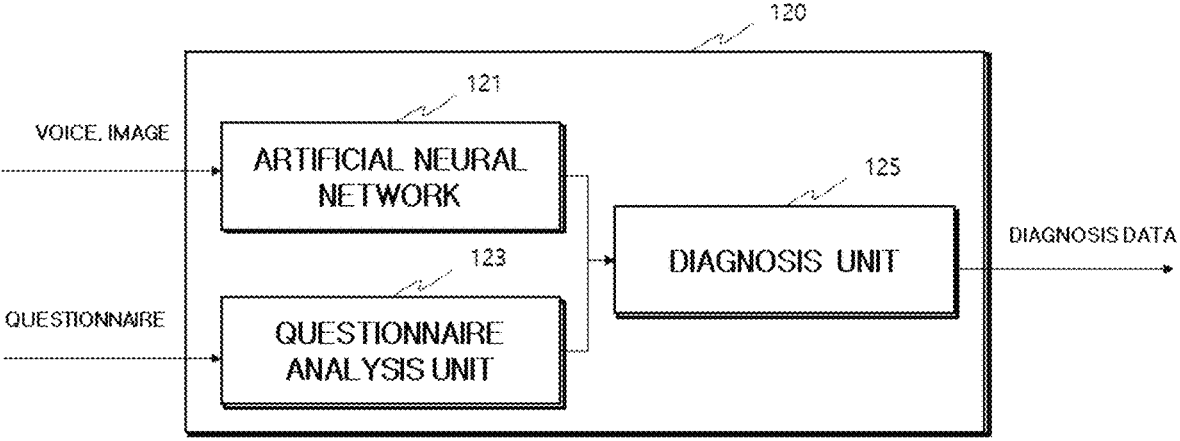
FIG. 3 is a configuration diagram of a control unit according to one exemplary embodiment.

According to one exemplary embodiment, the control unit 120 may receive at least one of image data and voice data for the analysis target from the user terminal 210 and perform first developmental disorder diagnosis through one or more artificial neural networks learned to perform developmental disorder diagnosis. Referring to FIG. 3, the control unit 120 may include one or more artificial neural networks 121 and may input the received image and voice data into the artificial neural network 121.

For example, the control unit 120 may obtain "developmental disorder observation and diagnosis data of other infants and toddlers by month" as training data in advance and use the training data to learn an artificial neural network. In this case, the training data may include image data and voice data for each of other infants and toddlers and questionnaire response data of the guardian. In addition, the diagnostic data on the degree of developmental disorder judged by a medical expert for each of other infants and toddlers is matched with the correct answer value so as to be included in the training data.

For example, the control unit 120 may use the artificial neural network model for the image data and voice data included in the training data to calculate a developmental disorder diagnosis prediction value for each of the predetermined developmental disorder items. For example, the artificial neural network may output a probability value or a predetermined score for each diagnosis item.

For example, the developmental disorder item may include at least one of i) large muscle/small muscle development, ii) social development, iii) cognitive ability development, and iv) language ability development. Here, the image data and voice data may be data obtained for the behavior and vocalization of infants and toddlers performing "a predetermined goal (for example, in the case of large muscle development, a large movement such as "jumping in place" is presented as a goal)" for each item of the degree of developmental disorder.

For example, the muscle development may be obtained by analyzing the degree of large muscle/small muscle use in the process of performing the target behavior, the social development may be obtained by analyzing the degree of mutual interaction with others (eye contact, number of attempts/ time for conversation, or the like), the cognitive ability development may be obtained by analyzing behavior and response speech to confirm concentration/memory, and the language ability development may be obtained by analyzing the fluency of sentence expression.

According to an example, the control unit 120 may include one artificial neural network capable of analyzing the muscle development, social development, cognitive development, and language development. As another example, the control unit 120 may include one or more artificial neural networks capable of analyzing the muscle development, social development, cognitive development, and language development, respectively.

According to an embodiment, the control unit 120 may receive the questionnaire response data from the user terminal 210 and perform second developmental disorder diagnosis according to predetermined standard. To this end, as illustrated in FIG. 3, the control unit 120 may include a questionnaire analysis unit 123. The questionnaire analysis unit 123 may derive diagnosis results for whether or not there is a developmental disorder and the degree of the developmental disorder based on the response score of each questionnaire item for the questionnaire response data. For example, the questionnaire analysis unit 123 may use a rule base that matches the diagnosis result corresponding to the standard when the score distribution for each item corresponds to a predetermined standard (rule). In this case, the questionnaire items may use questionnaire items of a developmental disorder diagnostic tool that is currently in use, such as the Korean Developmental Screening Test for Infants and Toddlers (K-DST).

The existing developmental disorder questionnaire has the following problems. The K-DST is a parent-report questionnaire evaluation, in which parents evaluate and submit developmental evaluation items of children to determine how proficient children are, and the parent questionnaire results are mainly used to determine whether the child's development is normal or delayed. However, since the standards for good performance by the parents are all different, the evaluation results are inconsistent. For example, some parents may think the children to be competent even if they succeed 6 out of 10 times, while others may think the children to be poor even if they succeed 6 out of 10 times. Alternatively, even if the same parent checks a question, there are questions that are considered proficient when the child succeeds 6 out of 10 times, and there are questions that are considered poor if the child succeeds 6 out of 10 times. Therefore, there may be inconsistencies in the questionnaire even if the same person checks it.

In addition, there are many cases where it is difficult to answer the questionnaire accurately because the level of understanding of the questions and developmental process varies greatly. For example, when it comes to climbing stairs, with respect to the question for whether a child can climb stairs while holding onto the railing, the parents check that the child can climb the stairs even when the child holds onto the railing with one hand and the bottoms of the stairs with the other hand. This is because parents do not know that if the children climb the stairs while holding onto the floor with their hands, it cannot be seen as the children climbing the stairs.

For example, in order to reduce the above errors, the control unit 120 may present to parents a numerical value for the standard of "can do well" (for example, 70 to 100%) and the standard of "sometimes possible" for the questionnaire evaluation. In addition, the control unit 120 may receive a video clip that allows observation of the developmental status by development evaluation area, and accurately judge the developmental status of the child from the perspective of an expert, thereby increasing accuracy compared to when only questionnaire evaluation is performed.

According to one exemplary embodiment, the control unit 120 may generate developmental disorder diagnosis data for the analysis target based on the first developmental disorder diagnosis and the second developmental disorder diagnosis. For example, as illustrated in FIG. 3, the control unit 120 may include a diagnosis unit 125, and the diagnosis unit 125 may generate the developmental disorder diagnosis data using the results derived by assigning predetermined weights to the first developmental disorder diagnosis and the second developmental disorder diagnosis, respectively.

According to one exemplary embodiment, the control unit 120 may transmit diagnosis guide data for developmental disorder diagnosis to the user terminal 210, and receive at least one of image data and voice data corresponding to the diagnosis guide data.

For example, the control unit 120 may provide guide information on the actions to be taken by the analysis target in order to diagnose the muscle development, and receive image data of the analysis target according to the guide. For another example, the control unit 120 may provide parents with the analysis target and a conversation performance guide to diagnose the social development, and receive image and voice data of the analysis target according to the guide.

According to one exemplary embodiment, the control unit may receive training data that includes at least one of the learning image data and learning voice data for one or more users using the artificial neural network and includes correct answer values for each of the learning image data and learning voice data to perform the first learning diagnosis, may perform the second learning diagnosis according to a predetermined standard based on one or more questionnaire training data, and may perform first learning of the artificial neural network by comparing the first learning diagnosis and the second learning diagnosis for the same person. For example, the control unit 120 may determine the consistency between the "developmental disorder diagnosis result of the artificial neural network" and the "developmental disorder diagnosis result based on the questionnaire response data" for the developmental disorder item.

According to one exemplary embodiment, when the first learning diagnosis and the second learning diagnosis for the same person are the same, the control unit 120 may update the artificial neural network using the corresponding learning image data and learning voice data. For example, when the two conclusions match, the control unit 120 may update the parameters of the artificial neural network so that the numerical data assigned to the developmental disorder item of the training data can be produced.

According to one exemplary embodiment, when the first learning diagnosis and the second learning diagnosis for the same person are different, and the correct answer value is compared with the first learning diagnosis and the second learning diagnosis for the same person and the first learning diagnosis is the same as the correct answer value, the control unit 120 may update the artificial neural network using the corresponding learning image data and learning voice data. Alternatively, when the first learning diagnosis and the second learning diagnosis for the same person are different, and the correct answer value is compared with the first learning diagnosis and the second learning diagnosis for the same person and the second learning diagnosis is the same as the correct answer value, the control unit 120 may exclude the corresponding learning image data and learning voice data from the training data.

For example, when the conclusion is inconsistent, the control unit 120 may use the diagnosis data of the medical expert as the "correct answer value" to check which data has different conclusions, and i) when the conclusion of the artificial neural network is derived close to the correct answer value, the artificial neural network may be updated, and ii) when only the conclusion of the questionnaire response data is derived close to the correct answer value, the corresponding training data of a specific other infant or toddler may be excluded from learning.

According to one exemplary embodiment, the control unit 120 may perform the first developmental disorder diagnosis on at least one of the image data and voice data for the analysis target received from the user terminal 210 using the first-learned artificial neural network, may perform the second developmental disorder diagnosis according to the predetermined standard based on the questionnaire response data received from the user terminal 210, and may generate the developmental disorder diagnosis data by assigning a predetermined weight to each of the first developmental disorder diagnosis and the second developmental disorder diagnosis.

According to one exemplary example, the control unit 120 may provide information on the "predetermined goal for judgment of a specific item among items for developmental disorder diagnosis" to the user terminal 210 of the guardian of the infant or toddler in a state where the artificial neural network is first learned. Thereafter, the control unit 120 may request the infant or toddler to be diagnosed to perform an action corresponding to the goal.

According to one exemplary example, the control unit 120 may obtain images and voice data of actions performed by the infant or toddler to be diagnosed to achieve the goal from the user terminal 210 of the guardian of the infant or toddler. The control unit 120 may perform a predetermined preprocessing on the acquired images and voice data of the infant or toddler to be diagnosed so that the first-learned artificial neural network can process the acquired images and voice data. For example, analog-to-digital conversion processing of the images and voice data, setting a region of interest (ROI) in the images to extract data of the corresponding regions, and removing unnecessary sections from the voice may be performed.

According to an example, the control unit 120 may perform a developmental disorder diagnosis on the infant or toddler to be diagnosed by applying the first-learned artificial neural network using the preprocessed data, thereby deriving the first developmental disorder diagnosis result. In addition, the control unit 120 may request responses to predetermined questionnaire items from the terminal of the guardian of the infant or toddler, obtain questionnaire response data entered by the guardian of the infant or toddler, and derive a second developmental disorder diagnosis result based on the questionnaire response data according to a predetermined rule (rule base).

Figure 4:
FIG. 4 is an example diagram of a developmental disorder diagnosis result according to one exemplary embodiment.

According to an example, the control unit 120 may synthesize the two results to derive the final developmental disorder diagnosis result. Referring to FIG. 4, in the developmental distribution statistics data of children of the same age as the infants and toddlers to be diagnosed for the final diagnosis result, the control unit 120 may express the results such as "i) borderline developmental delay, ii) developmental disorder findings, iii) average, and iv) above average (excellent) compared to peers", with a predetermined cutoff point (for example, standard deviation 00% borderline) as the standard.

The developmental disorder distribution statistics data of children of the same age may be utilized by inputting developmental disorder patient data investigated in advance, or the statistical values of the training data used in artificial neural network learning may be calculated and used. For example, when the training data of 1,000 other infants and toddlers is used in learning, the actual developmental disorder diagnosis distribution statistics data of the other infants and toddlers may be calculated and applied separately.

According to one exemplary embodiment, the control unit 120 may generate developmental disorder diagnosis data based on the first developmental disorder diagnosis when the first developmental disorder diagnosis and the second developmental disorder diagnosis are different. In addition, the control unit 120 may further generate notification data notifying that diagnosis results are different when the first developmental disorder diagnosis and the second developmental disorder diagnosis are different.

For example, a case where the first developmental disorder diagnosis and the second developmental disorder diagnosis are different includes a case where the score difference between the two diagnoses is outside a predetermined range or a case where two diagnosis results are derived differently from each other, as normal or disordered.

According to one example, when the first developmental disorder diagnosis result and the second developmental disorder diagnosis result are the same, the control unit 120 may assign a "predetermined weight" to each result to make the degree reflected in the final diagnosis result different. For example, when the first developmental disorder diagnosis and the second developmental disorder diagnosis are calculated as scores, the final diagnosis score may be calculated by assigning weights to each of the two scores.

According to an example, when the first developmental disorder diagnosis result and the second developmental disorder diagnosis result are different, the control unit 120 may determine the final developmental disorder diagnosis result using "developmental disorder diagnosis of artificial neural network" as the standard, and provide each diagnosis result to the user terminal 210 of the guardian of the infant or toddler to be diagnosed, along with a message that the two diagnosis results are different.

According to one exemplary embodiment, the control unit 120 may perform a re-diagnosis for items with different disorder diagnosis results when the first developmental disorder diagnosis and the second developmental disorder diagnosis are different. For example, the control unit 120 may perform a process that performs a "re-diagnosis" in relation to the corresponding diagnosis item. For example, in the case of the re-diagnosis process, overlapping processes among the previously performed processes may be omitted, and only data collection related to the corresponding diagnosis item may be additionally performed. For example, in the case of language developmental disorder, only providing a specific sentence utterance target and acquiring utterance voice data may be additionally performed. When the results of the re-diagnosis are also different, i) the re-diagnosis process may be repeated, or ii) information indicating that a precise diagnosis by a medical expert is required may be transmitted to the user terminal 210 of the guardian.

According to one exemplary embodiment, the control unit 120 may further receive disease data for the analysis target, and set the predetermined weight differently according to the disease data. For example, the control unit 120 may obtain a past disease history DB 310 for the infant or toddler to be diagnosed. In a case of deriving the final diagnosis result, when there is a history of a predetermined disease (for example, a history of a neuropsychiatric disease: ADHD, or the like) that may affect the diagnosis of developmental disorder, the control unit 120 may perform reflection to the diagnosis result and the final diagnosis result of the artificial neural network by adding a predetermined weight at the time of the final judgment. In other words, it may be diagnosed as having a higher possibility of developmental disorder.

According to one exemplary embodiment, the control unit 120 may transmit the image data, voice data, and question-naire response data for the analysis target received from the user terminal 210 to the user terminal 220 of the medical expert, may receive expert developmental disorder diagnosis data from the user terminal 220 of the medical expert, and may perform secondary learning of the artificial neural network using the first developmental disorder diagnosis when the first developmental disorder diagnosis and expert developmental disorder diagnosis are the same.

For example, when the final developmental disorder diag-nosis result for the infant or toddler to be diagnosed is derived, the control unit 120 provides i) observation data of the infant or toddler to be diagnosed, ii) questionnaire response data of the guardian, and iii) diagnosis result data to the user terminal 220 of the medical expert to request feedback on the developmental disorder, and may perform secondary learning on the first-learned artificial neural net-work with reference to the feedback.

For example, the final developmental disorder diagnosis result of the infant or toddler to be diagnosed, which reflects the diagnosis of the first-learned artificial neural network, and the feedback of the medical expert may be compared and analyzed as follows.

First AI model Positive=Medical expert True: TP (True-Positive)

First AI model Positive=Medical expert False: FP (False-Positive)

First AI model Negative=Medical expert False: FN (False-Negative)

First AI model Negative=Medical expert True: TN (True-Negative)

For example, the control unit 120 may use the observation data of infants and toddlers corresponding to "TP, FN", whose final developmental disorder diagnosis result reflect-ing the diagnosis of the first-learned artificial neural network is derived as the correct answer (medical expert feedback), the questionnaire response data of the guardian, the diag-nosis result data, and the feedback (correct answer sheet) data of the medical expert as additional training data to additionally learn the first-learned artificial neural network and build the secondary-learned artificial neural network.

According to one exemplary embodiment, the control unit 120 may derive a receiver operating characteristic (ROC) for the first-learned artificial neural network and an ROC for the second-learned artificial neural network, may maintain the first-learned artificial neural network when an area under the ROC Curve (AUC) of the first-learned artificial neural network is greater than an AUC of the second-learned artificial neural network, and may replace the first-learned artificial neural network with the second-learned artificial neural network when the AUC of the second-learned artifi-cial neural network is greater.

As an example, the control unit 120 may generate the ROC curve of the final developmental disorder diagnosis result data derived by re-inputting the training data of the infants and toddlers to be verified into the second-learned artificial neural network, and may calculate the AUC. The control unit 120 compares the first AUC of the first-learned artificial neural network with the second AUC of the second-learned artificial neural network, and i) when the second AUC>=the first AUC, the first-learned artificial neural net-work is replaced with the second-learned artificial neural network, and ii) when the second AUC<the first AUC, the first-learned artificial neural network may continue to be used. In this case, the control unit 120 may determine that the second-learned artificial neural network is incorrect.

Figure 5:
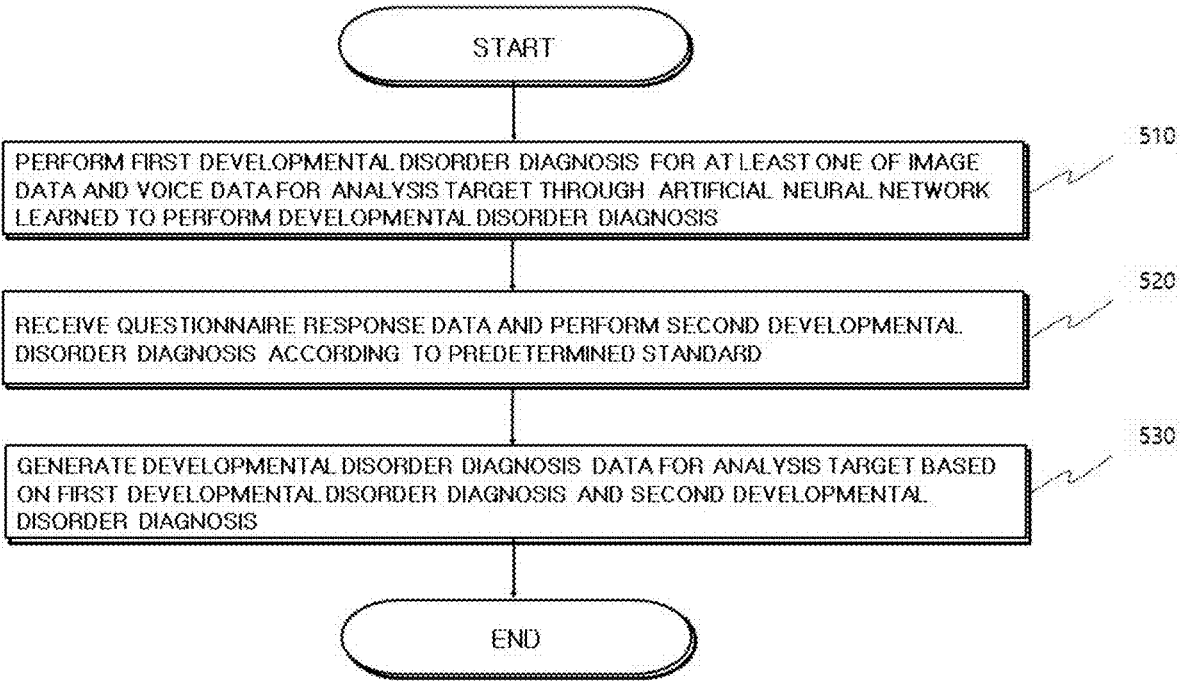
FIG. 5 is a flowchart illustrating a method for diagnosing developmental disorders according to one exemplary embodiment.

FIG. 5 is a flowchart illustrating a method for diagnosing developmental disorder according to one exemplary embodiment.

According to one exemplary embodiment, the apparatus for diagnosing developmental disorders may be a computing device having one or more processors and a memory storing one or more programs executed by the one or more proces-sors. The apparatus for diagnosing developmental disorders may receive at least one of image data and voice data for an analysis target from a user terminal and perform first devel-opmental disorder diagnosis through one or more artificial neural networks learned to perform the developmental dis-order diagnosis (510). In addition, the apparatus for diag-nosing developmental disorders may receive questionnaire response data from the user terminal and perform the second developmental disorder diagnosis according to predeter-mined standard (520). The apparatus for diagnosing devel-opmental disorders may generate the developmental disor-der diagnosis data for the analysis target based on the first developmental disorder diagnosis and the second develop-mental disorder diagnosis (530).

Exemplary embodiments that overlap with the contents described with reference to FIGS. 1 to 4 among the exem-plary embodiments of FIG. 5 are omitted.

One aspect of the present disclosure may be implemented as a computer-readable code on a computer-readable record-ing medium. Codes and code segments implementing the above program may be easily inferred by a computer pro-grammer in the art. The computer-readable recording medium may include all kinds of recording devices that store data that may be read by a computer system. Examples of the computer-readable recording medium may include ROM, RAM, CD-ROM, magnetic tape, floppy disk, optical disk, or the like. Additionally, the computer-readable record-ing medium may be distributed across network-connected computer systems, and may be written and executed as computer-readable code in a distributed manner.

The present disclosure has been examined so far, focusing on preferred exemplary embodiments thereof. Those skilled in the art will understand that the present disclosure can be implemented in modified forms without departing from the essential characteristics of the present disclosure. Accord-ingly, the scope of the present disclosure should not be limited to the above-described embodiments, but should be interpreted to include various exemplary embodiments within a scope equivalent to the contents described in the claims.

What is claimed is:

1. An apparatus for diagnosing developmental disorders, the apparatus comprising:

including one or more processors and a memory storing one or more programs executed by the one or more processors, wherein the control unit receives at least one of image data and voice data for an analysis target from one or more user terminals and performs a first developmental disorder diagnosis through one or more artificial neural networks learned to perform a developmental disorder diagnosis, receives questionnaire response data from the user terminal and performs a second developmental disorder diagnosis according to a predetermined standard, and generates developmental disorder diagnosis data for the analysis target by assigning predetermined weights to each of the first developmental disorder diagnosis and the second developmental disorder diagnosis and generating the final diagnosis based on the weighted diagnoses, wherein the control unit further receives training data that includes at least one of learning image data and learning voice data for one or more users using the artificial neural network and includes correct answer values for each of the learning image data and learning voice data to perform a first learning diagnosis, performs a second learning diagnosis according to a predetermined standard based on one or more questionnaire training data for the same person, and performs first learning of the artificial neural network by comparing the first learning diagnosis and the second learning diagnosis for the same person to determine consistency between a developmental disorder diagnosis result of the artificial neural network and a developmental disorder diagnosis result based on the questionnaire response data.

2. The apparatus of claim 1, wherein the control unit transmits diagnosis guide data for the developmental disorder diagnosis to the user terminal, the diagnosis guide data including guide information instructing the analysis target to perform predetermined actions or conversation tasks for diagnosing developmental disorder, and receives at least one of the image data and the voice data corresponding to the diagnosis guide data.

3. The apparatus of claim 1, wherein the control unit updates parameters of the artificial neural network using the corresponding the at least one of learning image data and learning voice data so that numerical data assigned to the developmental disorder item of the training data is produced based on the matched diagnoses when the first learning diagnosis and the second learning diagnosis for the same person are the same.

4. The apparatus of claim 1, wherein when the first learning diagnosis and the second learning diagnosis for the same person are different, and the correct answer value is compared with the first learning diagnosis and the second learning diagnosis for the same person, and when the first learning diagnosis is the same as the correct answer value, the control unit updates the artificial neural network using the corresponding learning image data and learning voice data.

5. The apparatus of claim 1, wherein when the first learning diagnosis and the second learning diagnosis for the same person are different, and the correct answer value is compared with the first learning diagnosis and the second learning diagnosis for the same person and the second learning diagnosis is the same as the correct answer value, the control unit excludes the corresponding learning image data and learning voice data from the training data.

6. The apparatus of claim 1, wherein the control unit performs the first developmental disorder diagnosis on at least one of the image data and the voice data for the analysis target received from the user terminal using the first-learned artificial neural network, performs the second developmental disorder diagnosis according to the predetermined standard based on the questionnaire response data received from the user terminal, and generates the developmental disorder diagnosis data by assigning a predetermined weight to each of the first developmental disorder diagnosis and the second developmental disorder diagnosis.

7. The apparatus of claim 6, wherein the control unit generates the developmental disorder diagnosis data based on the first developmental disorder diagnosis when the first developmental disorder diagnosis and the second developmental disorder diagnosis are different.

8. The apparatus of claim 7, wherein the control unit further generates notification data notifying that diagnosis results are different when the first developmental disorder diagnosis and the second developmental disorder diagnosis are different.

9. The apparatus of claim 7, wherein the control unit performs a re-diagnosis for items with different disorder diagnosis results when the first developmental disorder diagnosis and the second developmental disorder diagnosis are different.

10. The apparatus of claim 6, wherein the control unit further receives disease data for the analysis target, and sets the predetermined weight differently according to the disease data.

11. The apparatus of claim 6, wherein the control unit transmits the image data, voice data, and questionnaire response data for the analysis target received from the user terminal to a user terminal of a medical expert, receives expert developmental disorder diagnosis data from the user terminal of the medical expert, and performs secondary learning of the artificial neural network using the first developmental disorder diagnosis when the first developmental disorder diagnosis and the expert developmental disorder diagnosis are the same.

12. The apparatus of claim 11, wherein the control unit derives a receiver operating characteristic (ROC) for the first-learned artificial neural network and an ROC for the second-learned artificial neural network, maintains the first-learned artificial neural network when an area under the ROC Curve (AUC) of the first-learned artificial neural network is greater than an AUC of the second-learned artificial neural network, and replaces the first-learned artificial neural network with the second-learned artificial neural network when the AUC of the second-learned artificial neural network is greater.

13. A method for diagnosing developmental disorder performed by a computing device including one or more processors and a memory storing one or more programs executed by the one or more processors, the method comprising:

receiving at least one of image data and voice data for an analysis target from a user terminal and performing a first developmental disorder diagnosis through one or more artificial neural networks learned to perform a developmental disorder diagnosis;

receiving questionnaire response data from the user terminal and performing a second developmental disorder diagnosis according to a predetermined standard; and generating developmental disorder diagnosis data for the analysis target by assigning predetermined weights to each of the first developmental disorder diagnosis and the second developmental disorder diagnosis and generating the final diagnosis based on the weighted diagnoses, wherein the method further comprises:

receiving training data that includes at least one of learning image data and learning voice data for one or more users using the artificial neural network and includes correct answer values for each of the learning image data and learning voice data to perform a first learning diagnosis;

performing a second learning diagnosis according to a predetermined standard based on one or more questionnaire training data for the same person; and performing first learning of the artificial neural network by comparing the first learning diagnosis and the second learning diagnosis for the same person to determine consistency between a developmental disorder diagnosis result of the artificial neural network and a developmental disorder diagnosis result based on the questionnaire response data.

* * * * *